United States Patent
Kohut

[11] Patent Number: 5,911,686
[45] Date of Patent: Jun. 15, 1999

[54] MALE SEXUAL AID

[76] Inventor: Joseph Kohut, 126 Trowers Road, Woodbridge, Ontario, Canada, L4L 5Z4

[21] Appl. No.: 08/760,230

[22] Filed: Dec. 4, 1996

[30] Foreign Application Priority Data

Dec. 5, 1995 [CA] Canada ................................. 2164478

[51] Int. Cl.⁶ ...................................................... A61F 5/00
[52] U.S. Cl. ................................................ 600/38; 600/39
[58] Field of Search .................................... 128/845, 883; 600/38, 39, 41

[56] References Cited

U.S. PATENT DOCUMENTS

| | | |
|---|---|---|
| 3,511,230 | 5/1970 | Strong . |
| 4,262,662 | 4/1981 | Allinson . |
| 4,262,663 | 4/1981 | Allinson . |
| 4,362,152 | 12/1982 | Gorokhovsky et al. . |
| 4,440,183 | 4/1984 | Miller . |
| 4,643,175 | 2/1987 | Chapman . |
| 4,653,484 | 3/1987 | Cannon . |
| 4,672,954 | 6/1987 | Panzer ....................................... 600/39 |
| 4,785,802 | 11/1988 | Blount . |
| 4,872,447 | 10/1989 | Tsirjulnikov et al. ..................... 600/39 |
| 4,953,542 | 9/1990 | Tsirjulnikov et al. ..................... 600/39 |
| 5,065,744 | 11/1991 | Zusmanovsky ............................ 600/39 |
| 5,218,974 | 6/1993 | Garrett ..................................... 128/845 |

*Primary Examiner*—John P. Lacyk
*Assistant Examiner*—Rosiland Kearney
*Attorney, Agent, or Firm*—Neil H. Hughes; Ivor M. Hughes; Marcelo K. Sarkis

[57] ABSTRACT

A prosthesis for orienting a flacid penis in an orientation to accommodate sexual intercourse is provided. The prosthesis of the present invention does not interfere with the blood flow to the penis. A pair of continuous wire or rod shaped flexible members are formed separately and joined together to allow pivoting motion of the members with respect to one another in a pivoting relationship. The members are also coated with a flexible preferably soft latex like thermoplastic coating so as not to irritate the user. The prosthesis includes a the first engaging portion for engaging adjacent the glans of the penis, proximate the corona sulcus and the prosthesis also having laterally extending arms for engaging an area adjacent the public bone of the user for engaging with a securing strap to allow for the provision of various comfort positions. The prosthesis having disposed with each member intermediate the first and second ends, and disposed closer to the second end, a support for non interfering engagement adjacent the base of the penis proximate the sides thereof which do not interfere with the blood flow to the penis and together provide a prosthesis which will accommodate and support a flacid penis in an orientation to accommodate sexual intercourse. The members will rotate in relation to one another as the penis becomes engorged with blood while still supporting said penis, and not irritating the user or his sexual partner as a result of the preferred flexible thermoplastic coating, and the hinged rotary action of the members with respect to one another.

13 Claims, 6 Drawing Sheets

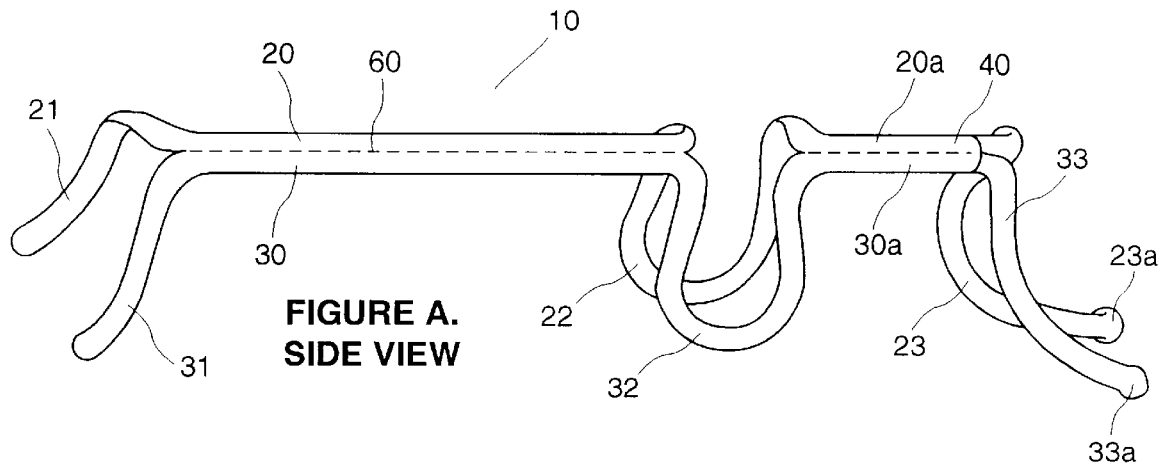
FIGURE A. SIDE VIEW
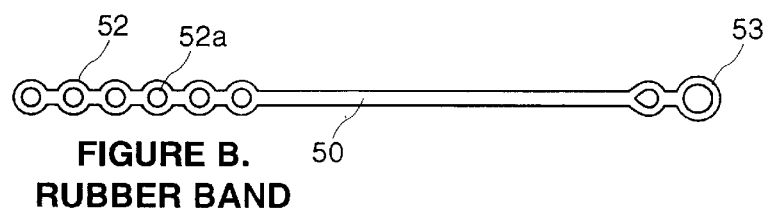
FIGURE B. RUBBER BAND
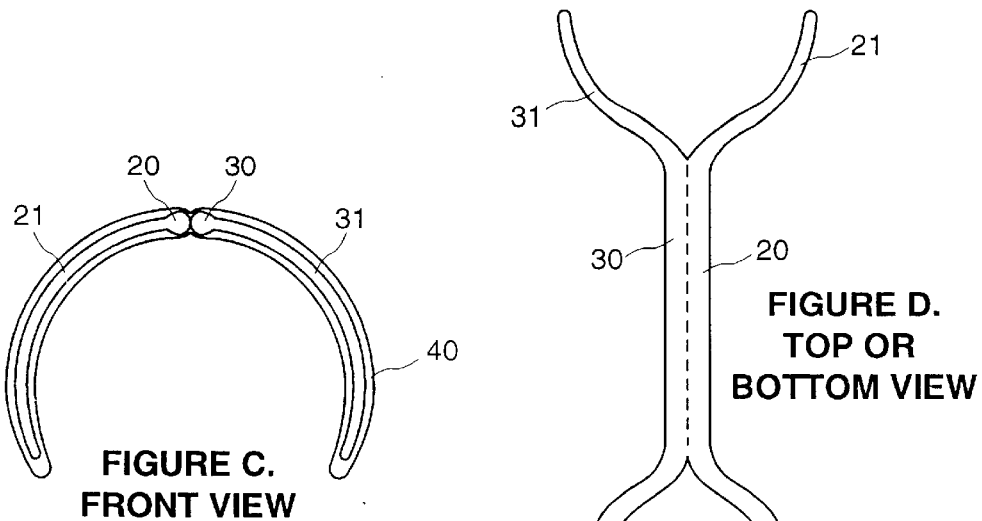
FIGURE C. FRONT VIEW
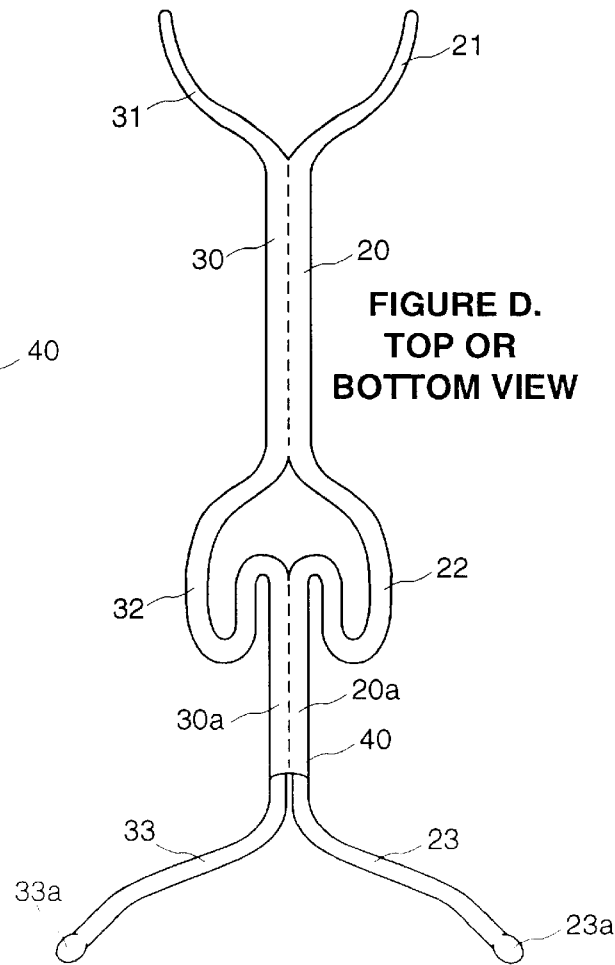
FIGURE D. TOP OR BOTTOM VIEW

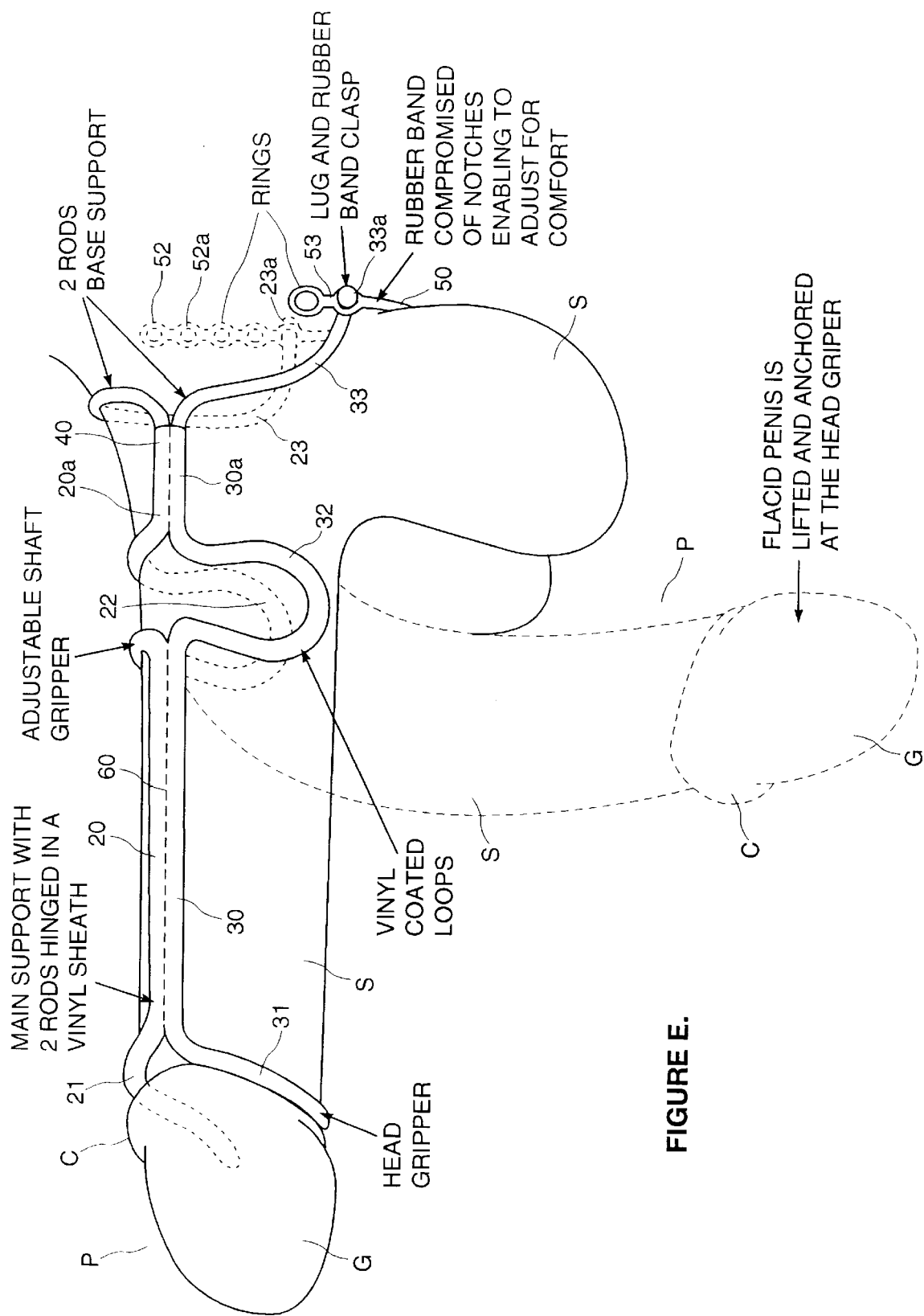
FIGURE E.

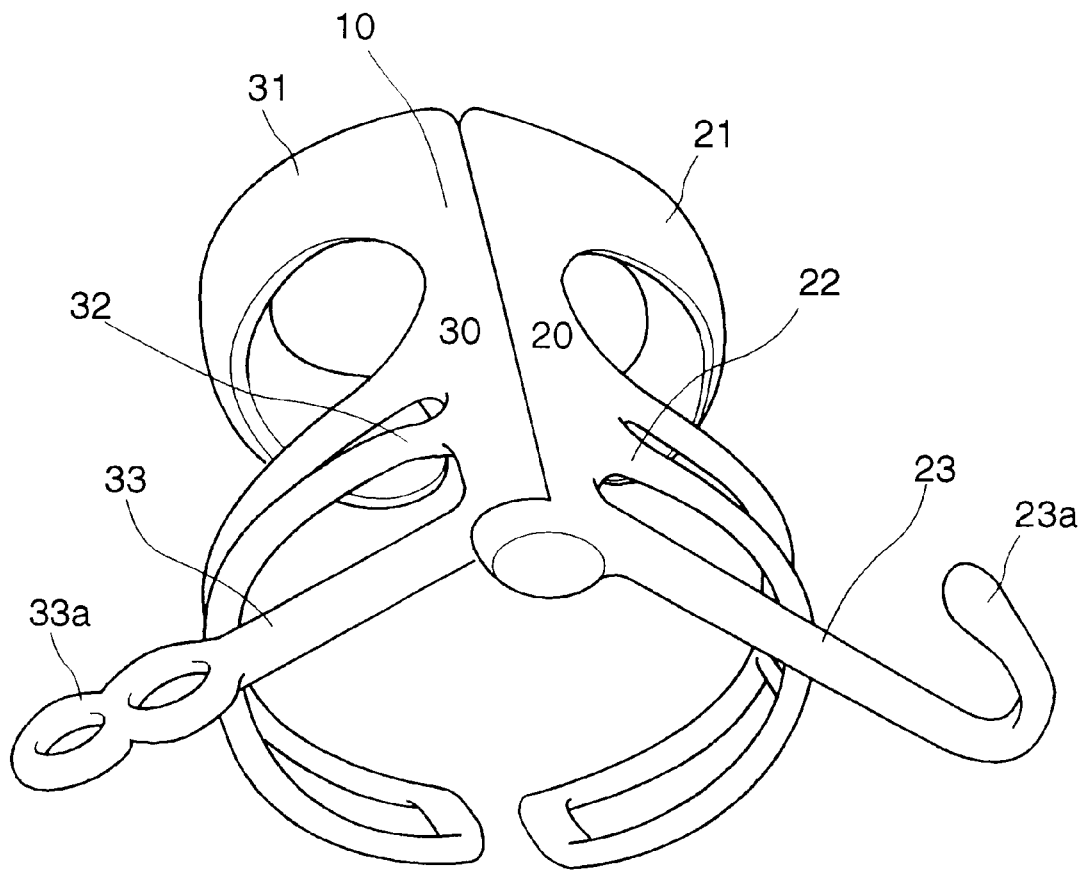
FIGURE F. BACK VIEW CLOSED

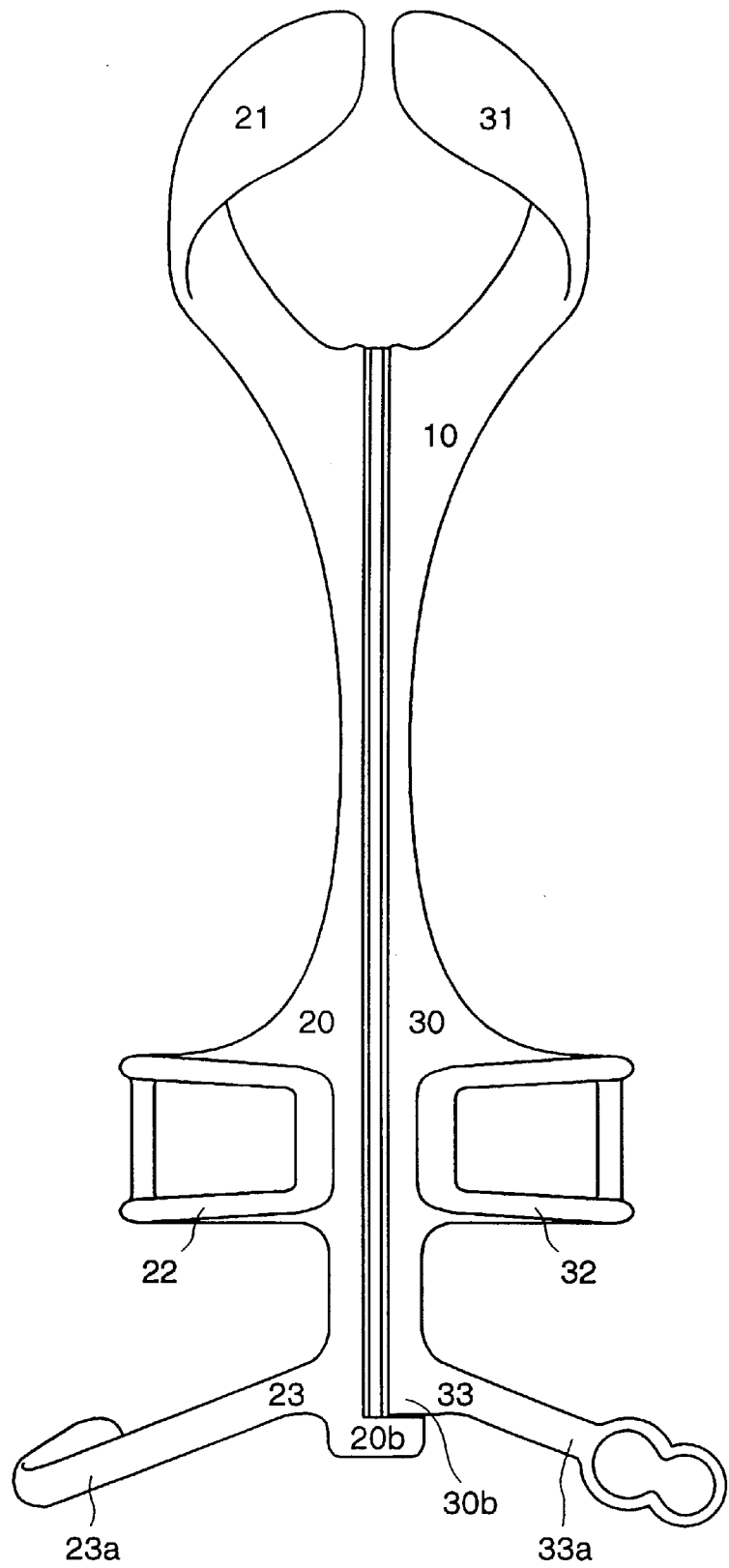
FIGURE G1   BOTTOM VIEW CLOSED

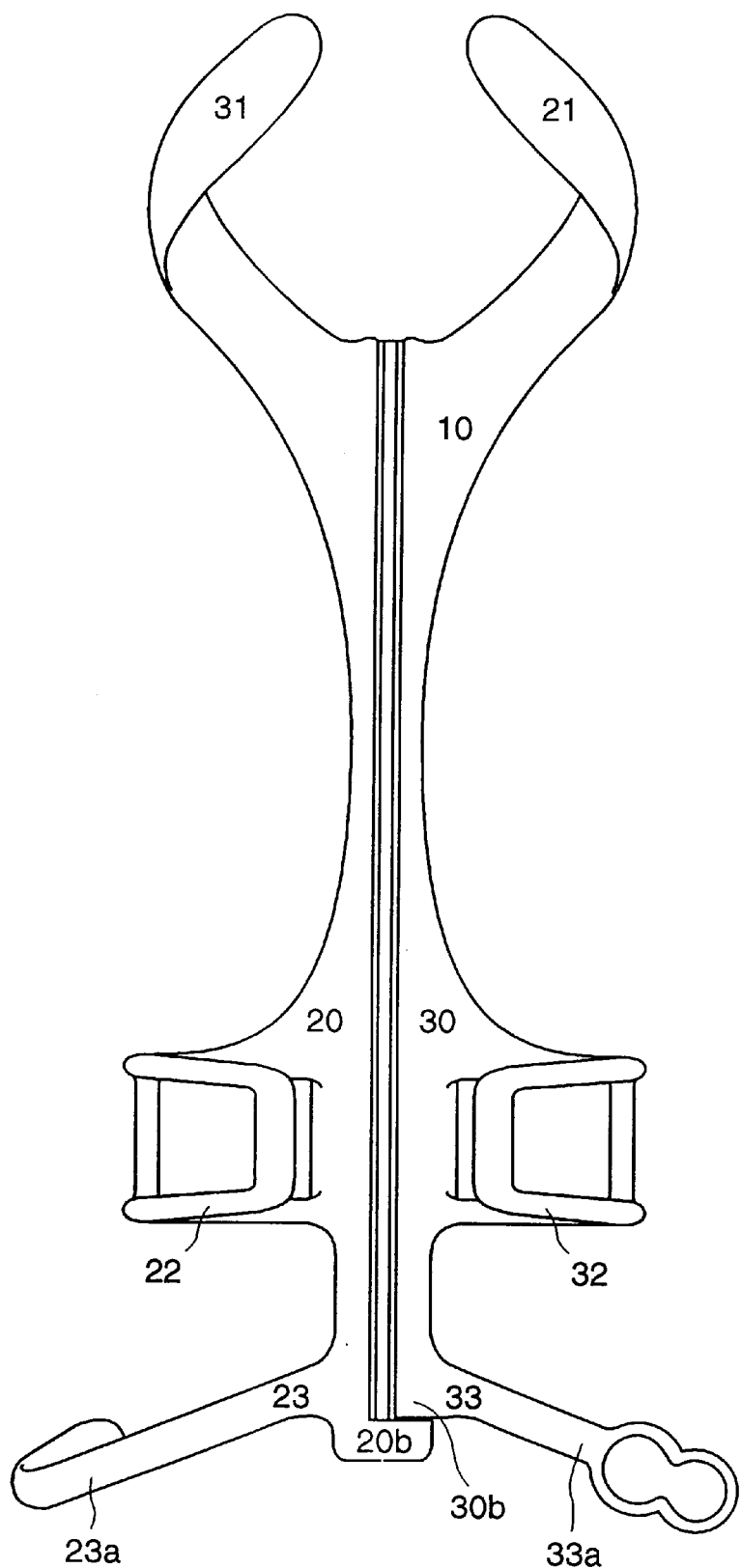
FIGURE G2 BOTTOM VIEW

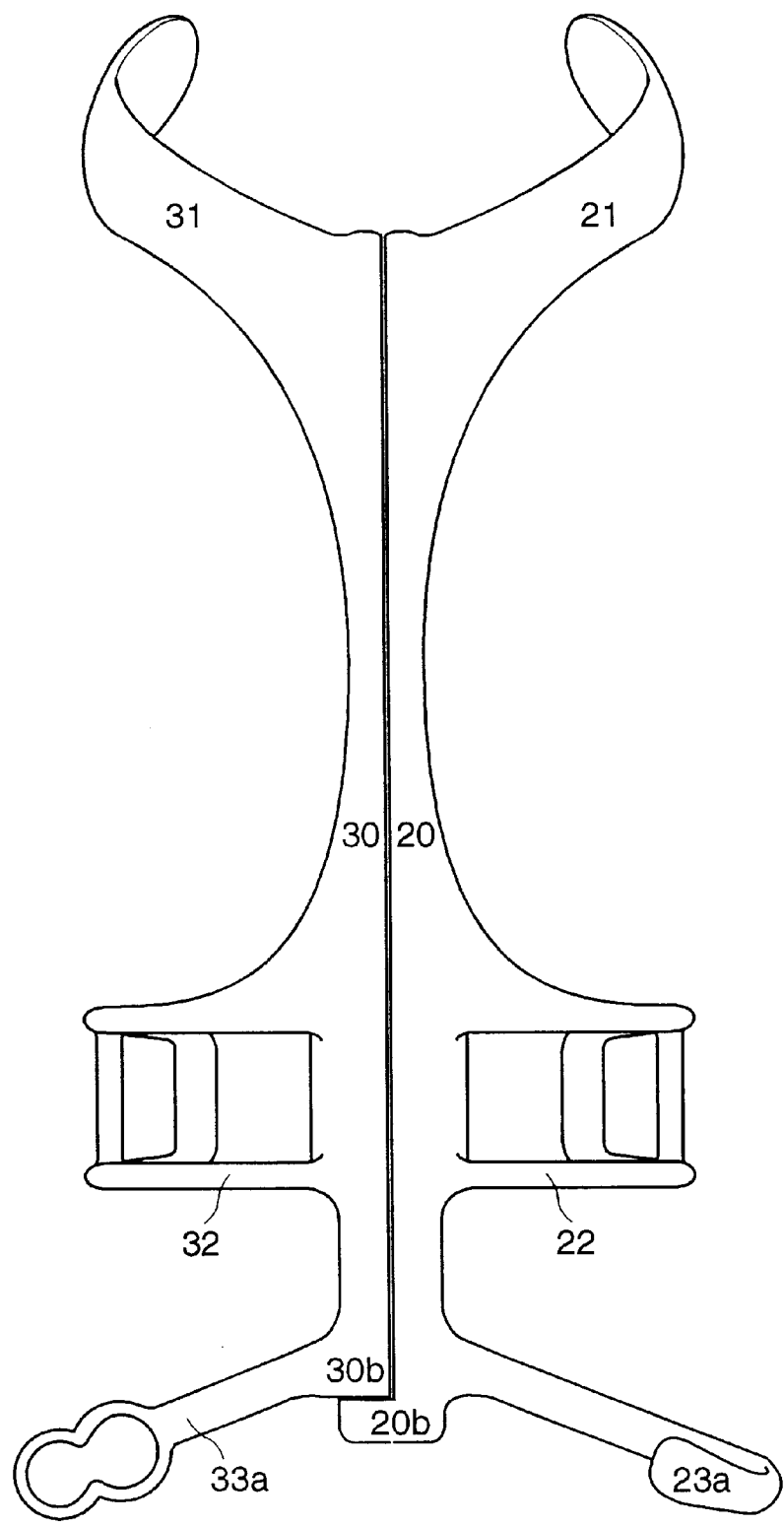
FIGURE H. TOP VIEW OPEN

MALE SEXUAL AID

FIELD OF THE INVENTION

This invention relates to a prosthesis for orienting a flaccid penis in an orientation to accommodate sexual intercourse and has particular application for those men suffering from impotency due to medical or psychological reasons.

REVIEW OF PRIOR ART

There are numerous devices available on the market place and in the prior literature which describe devices utilized by males in order to improve their abilities to participate in sexual intercourse. One such device well-known in the art provides for interfering with blood flow to the penis. This type of device is not recommended.

Many prior art structures such as U.S. Pat. No. 3,511,230 describe cutting off the supply of blood to the penis in order to maintain the blood trapped in the penis and prevent the organ from relaxing. It has been found that in utilizing devices such as that found within U.S. Pat. No. 3,511,230 or the like which effects the blood flow that there is a loss of sensation i.e. a numbness sets in the penis, as well as the penis turning blue. This is a direct result of blocking the dorsal vein in the penis.

Another more complicated device which also describes a prosthesis is taught in the U.S. Pat. No. 4,362,152. This device, although adjustable puts pressure on the dorsal vein as the penis becomes engorged with blood. The prosthetic has a pair of rigid rods which are encased in plastic in side by side relation having two ends. One end abuts the glans of the penis and the other end is located adjacent the pubic bone. However the prosthesis lacks a device or means to support the penis near the base thereof. When the penis becomes engorged with blood the two members tend to rotate in relation to one another causing the two ends adjacent the pubic bone to rotate toward each other, thereby applying pressure to the superficial dorsal vein of the penis and the corpora cavernosa. This device further lacks a stabilizer unit adjacent the base of the penis.

Another example of such a device is found in U.S. Pat. No. 4,653,484 which is relatively complicated to use and which describes a penile splint including an anchor which loops around the scrotum and in use exerts pressure at the base of the penis.

U.S. Pat. No. 4,262,662 describes a unitary member used as a support which is described at column 4 line 28 through 52. The use of the unit is quite awkward and difficult. Once in use it appears to be quite uncomfortable to wear and use.

Another example of a prosthetic device is found in U.S. Pat. No. 4,785,802 which includes a tail portion which extends between the legs of the user and further wherein portion 16 extends behind the scrotum and portion 18 engages the base of the penis. The support portions 14 acts like a splint as it extends along the underside of the penis. The unit appears to be very difficult to utilize. Similarly, U.S. Pat. No. 4,643,175 includes a very clumsy looking apparatus extending around the users waist and penis. U.S. Pat. No. 5,218,974 illustrates another device which is utilized to exert pressure including constrictors to limit the blood passage.

Another very clumsy appearing device in the prior art is taught in U.S. Pat. No. 4,440,183 which includes a diaper like item shown in FIG. 1, worn by the user in conjunction with the belted device. Finally, U.S. Pat. No. 4,262,663 provides for a penile support as seen in FIG. 5 which includes a one piece clip-on malleable penile prosthetic including a longitudinal support. However, it is evident that once this splint is positioned, when the penis becomes engorged with blood, the unit will although malleable cause some restriction at least to affect the comfort of the user.

Nowhere within the prior art is there found a prosthesis for orienting a flaccid penis to accommodate sexual intercourse which allows for dynamic adjustment as the user becomes sexually aroused, without interfering with the blood flow to the penis. The present invention can be worn and manipulated without constriction of the urethra or restraining blood flow to and from the corpora cavernosa or superficial dorsal vein.

It is therefore an object of this invention to provide a prosthetic device for assisting a male in participating in sexual intercourse which is comfortable to use and easy to wear.

It is a further object of this invention to provide a prosthetic device which is inexpensive to manufacture and purchase.

It is yet a further object of this invention to provide a prosthetic device which has various alternative comfort positions and will accommodate most males.

Further and other objects of the invention will become apparent to those skilled in the art when considering the following summary of the invention and a more detailed description of the preferred embodiments illustrated here.

SUMMARY OF THE INVENTION

According to a primary aspect of the invention, there is provided a prosthesis for orienting a flaccid penis in an orientation to accommodate sexual intercourse, said prosthesis not interfering with the blood flow to the penis and comprising a pair of continuous members, and preferably wire or rod shaped members, formed separately but joined together to allow pivoting motion of the members with respect to one another, preferably hinged together, and preferably coated with a flexible, preferably soft latex like, thermoplastic coating so as not to irritate the user, each member having a first and second end, the first end having disposed therewith a first engaging portion, the first engaging portion for engaging adjacent the glans of the penis, proximate the corona sulcus, and preferably being a pair of arcuate arms compatibly shaped with the glans of a penis to engage adjacent corona sulcus and preferably abutting the glans of the penis thereat, the second end of the members having disposed therewith laterally extending arms for engaging an area adjacent the pubic bone of the user and having provided proximate the ends of the arms, detents for engaging with a securing strap, and preferably being a hook shaped detent and/or an expanded knob-shaped detent for engagement with detents provide with the securing strap, and preferably eyelets and/or beads provided with the securing strap, to allow for the provision of various comfort positions in use, each member having disposed therewith intermediate the first and second ends, and disposed closer to the second end, a support for non interfering engagement adjacent the base of the penis proximate the sides thereof, wherein neither the supports nor the first engaging portions interfere with the blood flow to the penis and together provide a prosthesis which will accommodate and support a flaccid penis in an orientation to accommodate sexual intercourse, and which members during sexual intercourse will rotate in relation to one another as the penis becomes engorged with blood while still supporting said penis, and not irritating the user or his sexual partner, preferably as a result of, the preferred flexible thermoplastic coating, and the pivoting motion of the members with respect to one another.

BRIEF DESCRIPTION OF THE DRAWINGS

FIG. A is a side perspective view of the prosthetic device illustrated in a preferred embodiment of the invention.

FIG. B is a top view of the supporting strap indicating the various comfort positions and illustrated in a preferred embodiment of the invention.

FIG. C is a front view of the prosthetic device of FIG. A illustrated in the preferred embodiment of the invention.

FIG. D is a top view of the prosthetic device of FIG. A illustrated in a preferred embodiment of the invention.

FIG. E is a schematic view illustrating the use of the prosthetic device and illustrated in a preferred embodiment of the invention.

FIG. F is a back view of the prosthetic device illustrated in the preferred embodiment of the invention.

FIGS. G1 and G2 are bottom views in the intermediate and closed positions of the prosthetic device illustrated in the preferred embodiment of the invention.

FIG. H is a top open view of the prosthetic device illustrated in the preferred embodiment of the invention.

DETAILED DESCRIPTION OF THE PREFERRED EMBODIMENTS

Referring to the Figures there is illustrated a prosthetic device 10 which is best seen in FIG. E utilized to orient a flaccid penis P in a position as shown to accommodate sexual intercourse. The prosthetic device 10 therefore comprises two portions hinged together as best seen in FIG. H, items 20 and 30. Portions 20 and 30 are hinged together adjacent the end proximate the portions 30b and 20b. In one embodiment the hinge type device includes an opening in end 20b and a pin extending into the opening at 30b. The members 20 and 30 are coated with thermoplastic material together or individually. Alternatively coating the two members together in a sleeve of thermoplastic material provides a hinging action as long as the members 20 and 30 are free to rotate in a manner which will be herein described.

The prosthetic device therefore includes glans engaging portions 21 and 31 for engaging just behind the glans G of a penis P and preferably abutting the corona sulcus C as best seen in FIG. E. Each member 10 also includes a penis shaft engaging portions 22 and 32 for cooperatively engaging the sides of the penis adjacent the pubic bone to provide improved support. Unlike the prior art structures this added support will prevent the prosthesis from falling off in use. The supporting portions 22 and 32 are generally U-shaped and appear in FIG. F to encircle a flaccid penis and provide extra support proximate the base thereof. The members 20 and 30 include extension portions 20a and 30a which extend towards the pivots 30b and 20b wherein arms 23 and 33 are provided. Proximate each terminus of the arms 23 and 33 are detents 23a and 33a which may be as is shown in FIG. A or may be alternatively as provided in FIG. H. In either embodiment the rubber strap of FIG. B is utilized to engage detents 23a and 33a. As best seen in FIG. E the detent 53 of the rubber strap 50 is positioned so that the openings through 53 extend around the expanded bulbous end 33a of the arm 33.

When a user utilizes the prosthesis, the flaccid penis as seen in FIG. E is lifted into a supporting position so that the gripping portions 21 and 31 grip adjacent the glans G of the penis abutting the corona sulcus C. Since the gripping portions 21 and 31 of numbers 20 and 30 are coated with thermoplastic material which is flexible, there is no irritation to the user. The gripping portion 21 and 31 are adjusted by the user so as to secure the penis in position with the longitudinally extending portions of members 20 and 30 extending along the top of the penis P while the side supporting saddle-like members 22 and 32, as seen in FIG. E, or alternatively as seen in FIGS. G1 and G2 provide added support to both the sides and the bottom of the penis while the penis is in the flaccid condition. The end 52 of the strap is then pulled under the scrotum and attached to the detent 23a as shown in either FIG. A or as shown in FIG. H at the appropriate comfort position 52a for the user. The penis will now be fully supported in a flaccid condition as seen in FIG. E.

As best seen in FIG. F the prosthetic will therefore be in the closed position since in the flaccid condition the penis is not engorged with blood. However, the penis is now in the position to accommodate sexual intercourse. As the user becomes sexually aroused and blood engorges the penis, since the prosthetic of this invention does not in any way interfere with the blood flow to the penis, the glans of the penis will become engorged with blood as will the shaft. This will cause the pivoting or rotation of the gripping arms 21 and 31 and the side supporting members 22 and 32 in a direction laterally away from one another so as to adopt the position depending on the size of the penis of the individual user more closely resembling the open position shown in FIG. H. It can be readily seen in FIG. H that the gripping arms 31, 21 the side supporting arms 22, 32 and the end portions 23A and 33A all have been rotated in a direction away from one another when the prosthesis is in the open position. The strap therefore will ensure that the prosthesis stays snugly positioned at all times during sexual intercourse.

The prosthesis therefore allows for nature to take its course and for a man to be as naturally aroused as possible though impotent or suffering from other malaise. By orienting the penis and putting it in a position as shown, in FIG. E to accommodate sexual intercourse, and by providing a prosthetic device which is covered in a soft latex type rubber which would not in any way harm the user or his partner, that the prosthesis will allow for dynamic adjustment as the male is normally aroused during sexual relations with his partner. At no time is pressure placed on the penis or any other portion of the male anatomy. Further the strap is preferably made from inflexible materials so that an appropriate comfort position must be established prior to use. If the strap did stretch it would provide a corresponding force against the male anatomy which would not be recommended.

As many changes can be made to preferred embodiments of the invention without departing from the scope of the invention, it is intended that all contained herein be interpreted as illustrative of the invention and not in a limiting sense.

The embodiments of the invention in which an exclusive property or privilege is claimed are as follows:

1. A prosthesis for orienting a flaccid penis in an orientation to accommodate sexual intercourse, said prosthesis not interfering with the blood flow to the penis and comprising a pair of continuous members, formed separately but hinged together adjacent the ends of each member wherein an opening is disposed proximate one end of one of said members and a compatible pin is provided proximate the other end of one of said members, said pin extending into the opening and providing the hinge to allow pivoting motion of the members with respect to one another, each member having a first and second end, the first end having disposed therewith a first engaging portion, the first engaging portion for engaging adjacent the glans of the penis, proximate the corona sulcus, the second end of the members having disposed therewith laterally extending arms for engaging an area adjacent the pubic bone of the user and having provided proximate the ends of the arms detents for engaging with a securing strap to allow for the provision of various comfort positions in use, each member having disposed therewith intermediate the first and second ends, and disposed closer to the second end, a support for non interfering engagement adjacent the base of the penis proximate the sides thereof, wherein neither the supports nor the first engaging portions interfere with the blood flow to the penis and together provide a prosthesis which will accommodate and support a flaccid penis in an orientation to accommodate sexual intercourse, and which members during sexual intercourse will rotate in relation to one another as the penis becomes engorged with blood while still supporting said penis, and not irritating the user or his sexual partner, as a result of the pivoting motion of the members with respect to one another.

2. The prosthesis of claim 1 wherein the members are formed from and wire or rods.

3. The prosthesis of claim 1 wherein the members are coated with a flexible thermoplastic coating so as not to irritate the user.

4. The prosthesis of claim 3 wherein the first engaging portions of said members are a pair of arcuate arms compatibly shaped with the glans of a penis to engage adjacent corona sulcus.

5. The prosthesis of claim 3 wherein the members have disposed proximate the second end thereof hook shaped detents and/or expanded bulbous shaped detents for engagement with detents provide with a securing strap.

6. The prosthesis of claim 5 further comprising a securing strap having eyelets and/or beads provided therewith to engage the hook shaped detents and/or expanded bulbous shaped detents of each member to establish the various comfort positions.

7. The prosthesis of claim 1 or 2 wherein the first engaging portions of said members are a pair of arcuate arms compatibly shaped with the glans of a penis to engage adjacent corona sulcus.

8. The prosthesis of claim 7 wherein the members have disposed proximate the second end thereof hook shaped detents and/or expanded bulbous shaped detents for engagement with detents provide with a securing strap.

9. The prosthesis of claim 8 further comprising a securing strap having eyelets and/or beads provided therewith to engage the hook shaped detents and/or expanded bulbous shaped detents of each member to establish the various comfort positions.

10. The prosthesis of claim 1 or 2 wherein the members have disposed proximate the second end thereof hook shaped detents and/or expanded bulbous shaped detents for engagement with detents provide with a securing strap.

11. The prosthesis of claim 10 wherein the members have disposed proximate the second end thereof hook shaped detents and/or expanded bulbous shaped detents for engagement with detents provide with a securing strap.

12. The prosthesis of claim 11 further comprising a securing strap having eyelets and/or beads provided therewith to engage the hook shaped detents and/or expanded bulbous shaped detents of each member to establish the various comfort positions.

13. The prosthesis of claim 10 further comprising a securing strap having eyelets and/or beads provided therewith to engage the hook shaped detents and/or expanded bulbous shaped detents of each member to establish the various comfort positions.

* * * * *